United States Patent [19]
Benz et al.

[11] Patent Number: 5,577,093
[45] Date of Patent: *Nov. 19, 1996

[54] TARGET/STEM CONNECTION FOR X-RAY TUBE ANODE ASSEMBLIES

[75] Inventors: Mark G. Benz, Burnt Hills; Melvin R. Jackson, Niskayuna, both of N.Y.

[73] Assignee: General Electric Company, Schenectady, N.Y.

[*] Notice: The term of this patent shall not extend beyond the expiration date of Pat. No. 5,547,410.

[21] Appl. No.: 272,063

[22] Filed: Jul. 8, 1994

[51] Int. Cl.⁶ .................................................. H01J 35/10
[52] U.S. Cl. .................................... 378/125; 378/144
[58] Field of Search .............................. 378/119, 125, 378/130, 141, 143, 144, 199, 200, 202

[56] References Cited

U.S. PATENT DOCUMENTS

| | | | |
|---|---|---|---|
| 4,367,556 | 1/1983 | Hubner et al. | 378/144 |
| 4,574,388 | 3/1986 | Port et al. | 378/144 |
| 4,670,895 | 6/1987 | Penato et al. | 378/144 |
| 4,736,400 | 4/1988 | Koller et al. | 378/144 |
| 4,995,065 | 2/1991 | Janouin et al. | 378/130 |

*Primary Examiner*—Don Wong
*Attorney, Agent, or Firm*—R. Thomas Payne; William H. Pittman

[57] ABSTRACT

An improved high performance x-ray system having a rotating anode therein which includes an improved target/stem connection wherein at least about 40,000 x-ray scan-seconds are accomplished prior to tube failure due to anode assembly imbalance comprising a metallic target and a metal stem bonded to provide a composite rotating x-ray tube target is disclosed. An insert of an alloy, for example, tantalum alloy, is placed between the target layer and the stem and then bonded thereto to produce a composite x-ray tube target/stem having a high remelt temperature and bond strength which retains its balance throughout the manufacturing process and during x-ray tube operations is also disclosed.

23 Claims, 4 Drawing Sheets

TARGET/STEM CONNECTION FOR X-RAY TUBE ANODE ASSEMBLIES

RELATED APPLICATIONS

This application is related to commonly assigned U.S. patent application Ser. No. 08/272,065 (RD-23,773) of Eggleston et al., filed Jul. 8, 1994, and U.S. patent application Ser. No. 08/272,064 (RD-23,774) of Eggleston et al., filed Jul. 8, 1994, and incorporated by reference herein.

BACKGROUND OF THE INVENTION

The present invention relates to equipment for diagnostic and therapeutic radiology and methods of making the same and, more particularly, to high performance targets used in x-ray generating equipment, such as computerized axial tomography (C.A.T.) scanners. More particularly, the invention is directed to high performance rotating x-ray tube anode structures having metal to metal bonding between the target and stem and methods of making same. Most particularly, it relates to the joining of the molybdenum-alloy disk to the niobium alloy anode stem portion wherein tantalum alloy inserts are used as the bonding material.

X-ray tube performance can be affected by the balance of the anode assembly. Specifically, during x-ray tube manufacturing, it is important to be able to balance the anode assembly and have it stay balanced during completion of the manufacturing cycle and during operation of the x-ray tube. As the size of x-ray tube targets has increased to six and one half inch (6½") and beyond, it has proved difficult to maintain this balance and thus, reduced manufacturing yields and shortened operational lives have been experienced. Field evaluation of failed x-ray tubes has indicated that the imbalance of the anode assembly has occurred in the region of the attachment of the target to the stem or shaft.

In producing new and improved targets for rotary anode x-ray application, it is not only necessary for the target/stem connection to survive a more rigorous environment in the x-ray tube but it must also be able to survive more rigorous manufacturing processes such as the vacuum firing at temperatures up to about 1500 degree(s) C. This requires that the improved connection provide the following benefits:

1. The bonding temperature be low enough to not adversely affect the properties of the TZM alloy which can lose significant strength at about 2000 degree(s) C.

2. After bonding, have sufficient high temperature strength to support the bond through the additional manufacturing steps such as vacuum firing to about 1500 degree(s) C.

3. The bond should be strong and should not be degraded by thermal excursions during normal x-ray tube operation up to 1500 degree(s) C. for extended periods of time.

For a particular set of bonding metals, such as in diffusion bonding, to work under the above parameters, it must have certain inherent properties. The first would be that the metals do not have a eutectic or peritectic reaction with the TZM target layer. Ultimately, the bond metals used, such as in diffusion bonding, should form only a simple binary solid solution with the molybdenum in the TZM alloy.

A basic rule in bonding dissimilar materials is that for a bond to occur there must be some intermixing of the elements between the two materials. Also, for this bond to have significant strength, the gradation of intermixing should approximate that of a binary diffusion couple where the two materials diffuse together in equal portions.

Conventional stem/shaft connections, to the extent they may be viable in conventional x-ray imaging systems, face a much more severe test in connection with the use of graphite members in x-ray tubes used in medical computerized axial tomography (C.A.T.) scanners. For the formation of images, a medical C.A.T. scanner typically requires an x-ray beam of about 2 to 8 seconds duration. Such exposure times are much longer than the fractions-of-a-second exposure times typical for conventional x-ray imaging systems. As a result of these increased exposure times, a much larger amount of heat (generated as a by-product of the process of x-ray generation in the target region) must be stored and eventually dissipated by the rotating anode.

Recently, the problem related to anode assembly failure due to imbalance reached a critical point. Due to the tremendous stresses undergone by the larger diameter x-ray tubes during continuous operation, the average tube life had been approximately 30,000 scan-seconds, utilizing the conventional threaded stem, Belleville washer mechanical connection. Since approximately 20% of the failures were related to anode assembly imbalance, the need for an improved anode assembly having a more durable target/stem connection that would eliminate the imbalance while maintaining the effectiveness of the target became apparent. Such an anode assembly desirably would provide sufficient balance during the operation life of the target while reducing significantly, if not eliminating, entirely anode assembly balance problems.

SUMMARY OF THE INVENTION

In carrying out the present invention in preferred forms thereof, we provide an improved x-ray anode assembly for use in x-ray tubes, such as those incorporated in diagnostic and therapeutic radiology machines, for example, computer tomography scanners. Illustrated embodiments of the invention disclosed herein, are in the form of x-ray systems having an x-ray tube which includes the improved anode assembly.

Each x-ray tube is normally enclosed in an oil-filled protective casing. A glass envelope contains a cathode plate, a rotating disk target and a rotor that is part of a motor assembly that spins the target. A stator is provided outside the tube proximate to the rotor and overlapping therewith about two-thirds of the rotor length. The glass envelope is enclosed in an oil-filled lead casing having a window for the x-rays that are generated to escape the tube. The casing in some x-ray tubes may include an expansion vessel, such as a bellows.

X-rays are produced when, in a vacuum, electrons are released, accelerated and then abruptly stopped. This takes place in the x-ray tube. To release electrons, the filament in the tube is heated to incandescence (white heat) by passing an electric current through it. The electrons are accelerated by a high voltage (ranging from about ten thousand to in excess of hundreds of thousands of volts) between the anode (positive) and the cathode (negative) and impinge on the anode, whereby they are abruptly slowed down. The anode, usually referred to as the target, is often of the rotating disc type, so that the electron beam is constantly striking a different point on the anode perimeter. The x-ray tube itself is made of glass, but is enclosed in a protective casing that is filled with oil to absorb the heat produced. High voltages for operating the tube are supplied by a transformer. The alternating current is rectified by means of rectifier tubes (or "valves") in some cases by means of barrier-layered rectifiers.

For therapeutic purposes—e.g., the treatment of tumors, etc.—the x-rays employed are in some cases generated at much higher voltages (over 4,000,000 volts). Also, the rays emitted by radium and artificial radiotropics, as well as electrons, neutrons and other high speed particles (for instance produced by a betatron), are used in radio therapy.

In one specific embodiment of the present invention, an x-ray tube comprising: a glass envelope; a cathode operatively positioned in the glass envelope; an anode assembly including a rotor, a stator, operatively positioned relative to the rotor, and a target operatively positioned relative to the cathode and operatively connected to the rotor by metal to metal diffusion bonding between the target and a metal insert and metal to metal bonding of the insert to a stem.

Another aspect of the present invention is embodied in an x-ray tube having a stem/target connection such that at least about 40,000 x-ray scan-seconds are accomplished prior to tube failure due to rotor imbalance.

Another aspect of the present invention is embodied in an x-ray system comprising: an enclosure having oil contained therein; an oil pump, operatively positioned relative to the enclosure for circulating oil within the system; at least one cooling means, operatively connected to the enclosure and the oil pump, for cooling the oil; an x-ray tube, operatively positioned inside the enclosure, for generating the x-rays, the x-ray tube comprising: a glass envelope; a cathode, operatively positioned in the glass frame; an anode assembly including a rotor, a stator, operatively positioned relative to the rotor, and a target, operatively positioned relative to the cathode and operatively connected to a stem by metal to metal diffusion bonding between the target and a metal insert and metal to metal bonding between the insert and a stem.

Another aspect of the present invention is embodied in an x-ray system having a stem/target connection such that at least about 40,000 x-ray scan-seconds are accomplished before tube failure due to anode assembly imbalance.

In one specific embodiment of the present invention, the target is diffusion bonded to the niobium alloy stem utilizing a tantalum bond alloy.

Briefly, in accordance with one aspect of the present invention there is provided an x-ray system having an x-ray tube including a metallic target and a stem bonded together to result in a composite rotating x-ray tube target. In another aspect of the present invention, an insert of a tantalum based alloy is co-produced with the metallic target during manufacture of the target. The processing produces a diffusion bond between the insert and the stem. It is desirable that the insert be a powder alloy compatible with the processing steps used in the manufacture of the target such as, for example, powder making, die pressing, sintering, forging, annealing, and coating or brazing to a graphite back. Such a material should be able to maintain a small grain size, high strength and good ductility during this combination of process steps, such as, for example, Ta. The insert material could also be chosen from the group comprising: Ta-10W (Ta, 10W); T-111 (Ta, 8W, 2Hf); T-222 (Ta, 9.6W, 2.4Hf, 0.01C); ASTAR-811C (Ta, 8W, 1Re, 1Hf, 0.025C); GE-473 (Ta, 7W, 3Re); Ta-2.5W (Ta, 2.5W); and Ta-130 (Ta with 50–200 ppm Y). The stem or stud is manufactured from a Nb-based alloy, to take advantage of the combination of high strength and low thermal conductivity such as, for example, Nb. The stem material could also be chosen from a group comprising: CB-752 (Nb, 10W, 2.5Zr); C129Y (Nb, 10W, 10Hf, 0.1Y); FS-85 (Nb, 28Ta, 11W, 0.8Zr); and C103 (Nb, 10, Hf, 1Ti, 0.7Zr). C103 is preferred.

In one possible combination, the stem and insert are slightly tapered so that sufficient contact pressure between the two is established to facilitate the diffusion bonding therebetween. This pressure is preferably provided for press-fitting the stem into the target. The diffusion bonding between the stem and the target via the insert is preferably accomplished by vacuum annealing for a sufficient time (about 3 hours) at a sufficient temperature (preferably higher than 1150° C.) and at a sufficient contact pressure (preferably greater than 10,000 psi) to effectuate diffusion bonding.

Accordingly, an object of the present invention is to provide an x-ray system including an improved x-ray tube having increased scan life.

Another object of the present invention is to provide an improved x-ray tube having a scan life of at least 40,000 scan-seconds.

A further object of the present invention is to provide an x-ray tube having an improved anode assembly which maintains proper balance during the life of the tube.

A still further object of the present invention is to provide a metal to metal bonded connection between the target and the stem that will prevent anode assembly imbalance for at least 40,000 scan-seconds.

Another object of the present invention is to provide a target stem attachment configuration having fewer parts.

Other objects and advantages of the invention will be apparent from the following description, the accompanying drawings and the appended claims.

BRIEF DESCRIPTION OF THE DRAWINGS

FIG. 1b is a sectional view with parts removed of the x-ray system of FIG. 1a;

DESCRIPTION OF THE PREFERRED EMBODIMENT

Figure 1A:
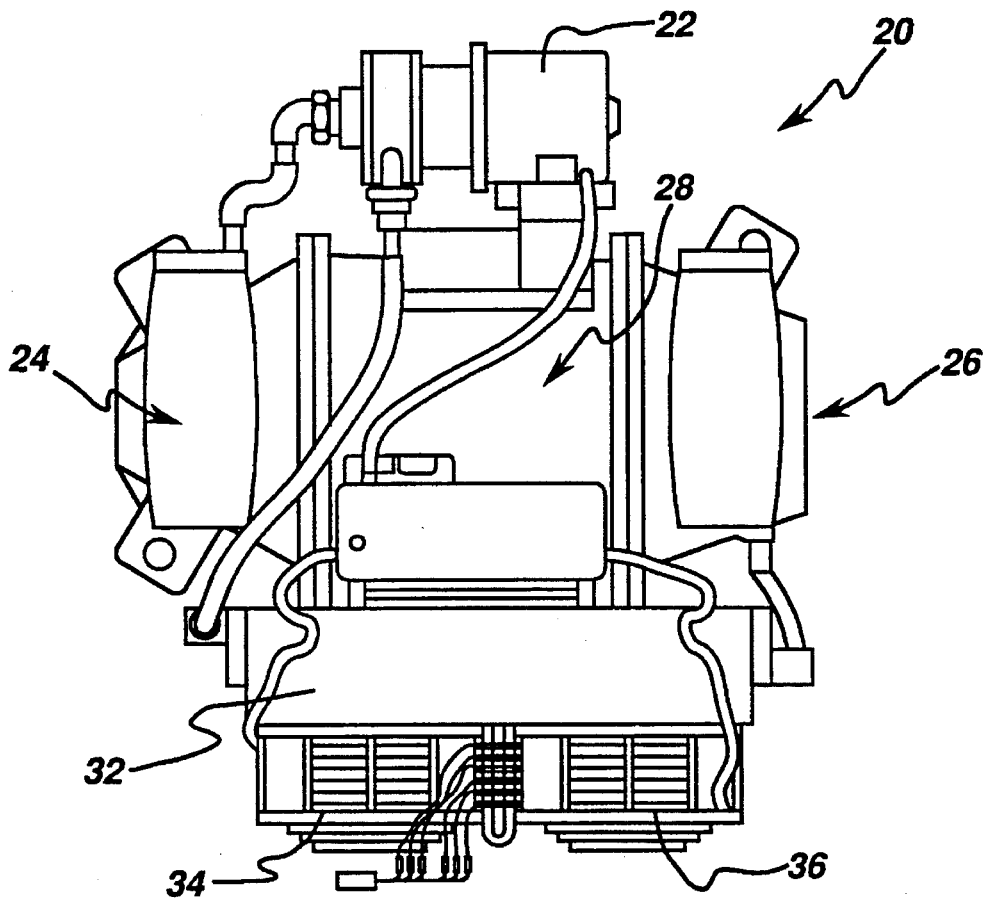
FIG. 1a is a plan view of a representative x-ray system.
Figure 1B:
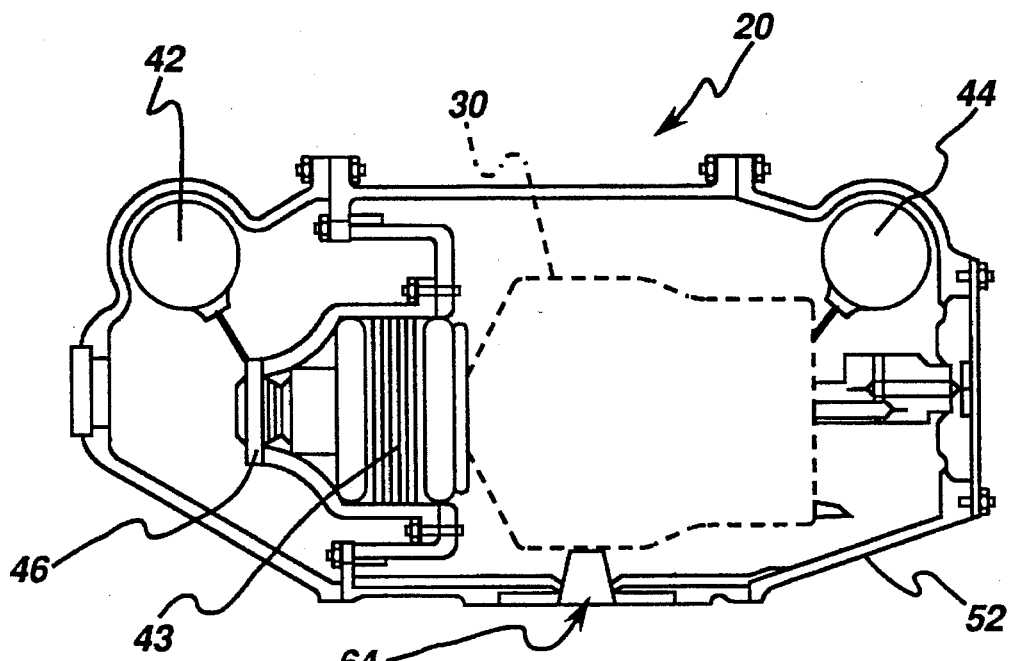
Figure 2:
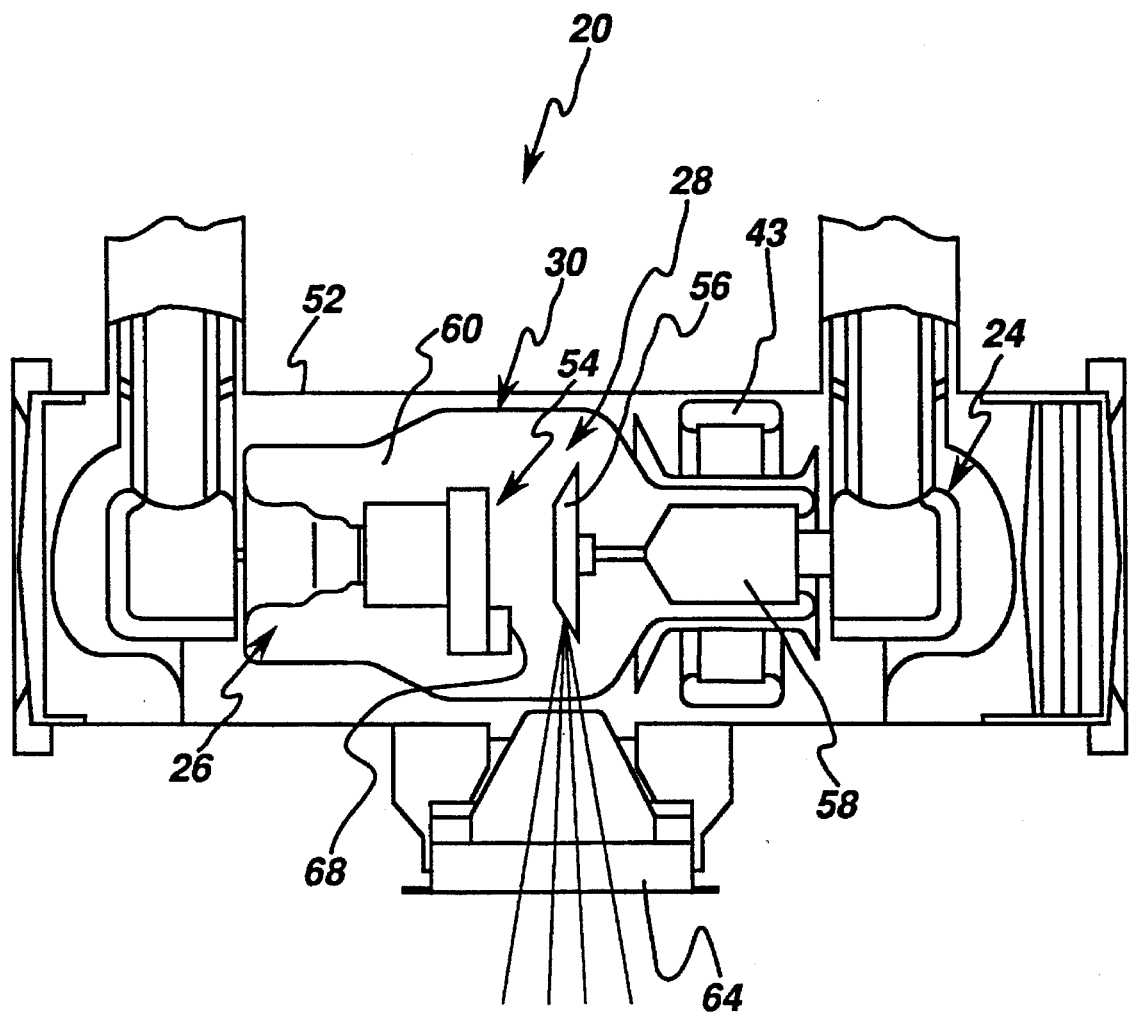
FIG. 2 is a schematic representation of another representative x-ray system having an x-ray tube positioned therein.

A representative x-ray system embodying the present invention in one preferred form thereof is illustrated as generally designated by the numeral 20 in FIGS. 1a, 1b and 2. As can be seen, the system 20 comprises an oil pump 22, an anode end 24, a cathode end 26, a center section 28 positioned between the anode end and the cathode end, which contains the x-ray tube 30. A radiator 32 for cooling the oil is positioned to one side of the center section and may have fans 34 and 36 operatively connected to the radiator 32 for providing cooling air flow over the radiator as the hot oil circulates therethrough. The oil pump 22 is provided for circulating the hot oil through the system 20 and through the radiator 32, etc. As shown in FIG. 1b, electrical connections are provided in the anode receptacle 42 and the cathode receptacle 44.

As shown in FIG. 2, the x-ray system 20 comprises a casing 52 preferably made of aluminum and lined with lead and a cathode plate 54, a rotating target disc 56 and a rotor 58 enclosed in a glass envelope 60. A stator 43 is positioned outside the glass envelope 60 inside the lead lined casing 52 relative to the rotor 58. The casing 52 is filled with oil for cooling and high voltage insulation purposes as was explained above. A window 64 for emitting x-rays is operatively formed in the casing 52 and relative to the target disc 56 for allowing generated x-rays to exit the x-ray system 20.

Figure 3:
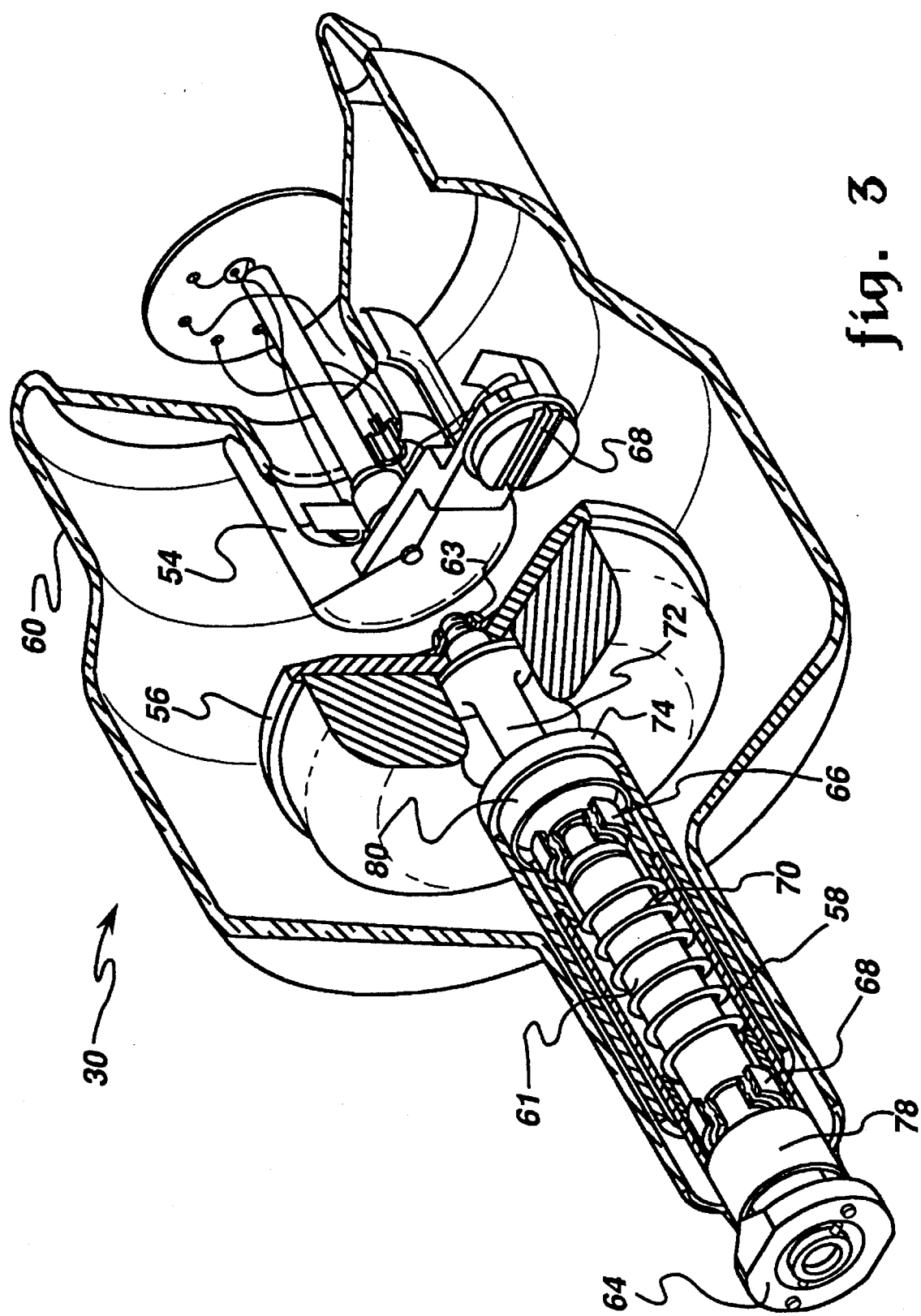
FIG. 3 is a partial perspective view of a representative x-ray tube with parts removed, parts in section, and parts broken away.

Referring to FIG. 3, there is shown the cathode 54 positioned inside the glass envelope 60. As is well known, inside the glass envelope there is a vacuum of about $10^{-5}$ to about $10^{-9}$ torr. The electricity generates x-rays that are aimed from the cathode filament 68 to the anode target or the top of the target disc 56. The target disc is conventionally connected to a rotating shaft 61 at one end by a Belleville nut 63 and by another nut at the other end 64. A front bearing 66 and a rear bearing 68 are operatively positioned on the shaft 61 and are held in position in a conventional manner. The bearings 66 and 68 are usually lubricated and are susceptible to failure at high operating temperatures.

A preload spring 70 is positioned about the shaft 61 between the bearings 66, 68 for maintaining load on the bearings during expansion and contraction of the anode assembly. A rotor stud 72 is utilized to space the end of the rotor most proximate the target 56 from the rotor hub 74. The bearings, both front 66 and rear 68, are held in place by bearing retainers 78 and 80. The rotor assembly also includes a stem ring and a stem, all of which help to provide for the rotation of the rotor 58 with the target 56.

The temperature in the area of the filament 68 can get as high as about 2500° C. Other temperatures include about 1100° C. near the center of the rotating target 56, which rotates at about 10,000 rpm. Temperatures of the focal spot on the target 56 can approximate 3200° C. and temperatures on the outside edge of the rotating target 56 approach about 1300° C. The temperature in the area of the rotor hub 74 approaches 700° C. and of the front bearing approaches 450° C. maximum. Obviously, as one moves from the target 56 to the rotor 58 and stator 43, the temperature appears to decrease.

During operation of some x-ray systems having larger diameter targets, severe protocol users have maximized usage of the system by making as many scans at high peak power in as short a time as possible. One of the problems with utilizing any x-ray system in this continuous type of operation is the amount of heat that is generated, which may in fact destroy the bearings 66, 68, especially the front bearing 66.

If the x-ray tube target 56 and rotor 58 were allowed to continue to rotate at 10,000 rpm between scans, the bearings would wear out prematurely and cause the tube to fail. Thus, if it appears that there would be more than 60 seconds between scans, the x-ray system operating control system software is programmed to brake the rotor by rapidly slowing it completely down to zero (0) rpm. However, when ready to initiate a scan, the control system software is programmed to return the target and the rotor to 10,000 rpm as quickly as possible. These rapid accelerations and brakes are utilized because, among other reasons, there are a number of resonant frequencies that must be avoided during the acceleration from zero (0) to 10,000 rpm and the brake from 10,000 rpm to zero (0) rpm. In order to pass through these resonant frequencies both immediately before a scan or a series of scans and after a scan or series of scans as fast as possible, the x-ray system applies maximum power to bring the target, or anode, to 10,000 rpm or down to zero (0) rpm in the least amount of time possible.

It should be noted that the x-ray tube target and rotor can be accelerated to 10,000 rpm from a dead stop in about 12 to about 15 seconds and slowed down at about the same rate. Vibration from the resonant frequencies is a problem, if the tube is allowed to spin to a stop without braking.

It has been found that during these rapid accelerations to 10,000 rpm and the immediate braking from 10,000 rpm to zero, stresses, mechanical as well as thermal, impact on the rotor 58 and the target/stem connection. These stresses may contribute to anode assembly imbalance which is believed to have caused premature failure in about twenty (20) percent of recent GE x-ray tube failures. It has been determined that these imbalance problems are most likely caused by changes that occur in the area of the target 56/stem 84 attachment.

Figure 4:
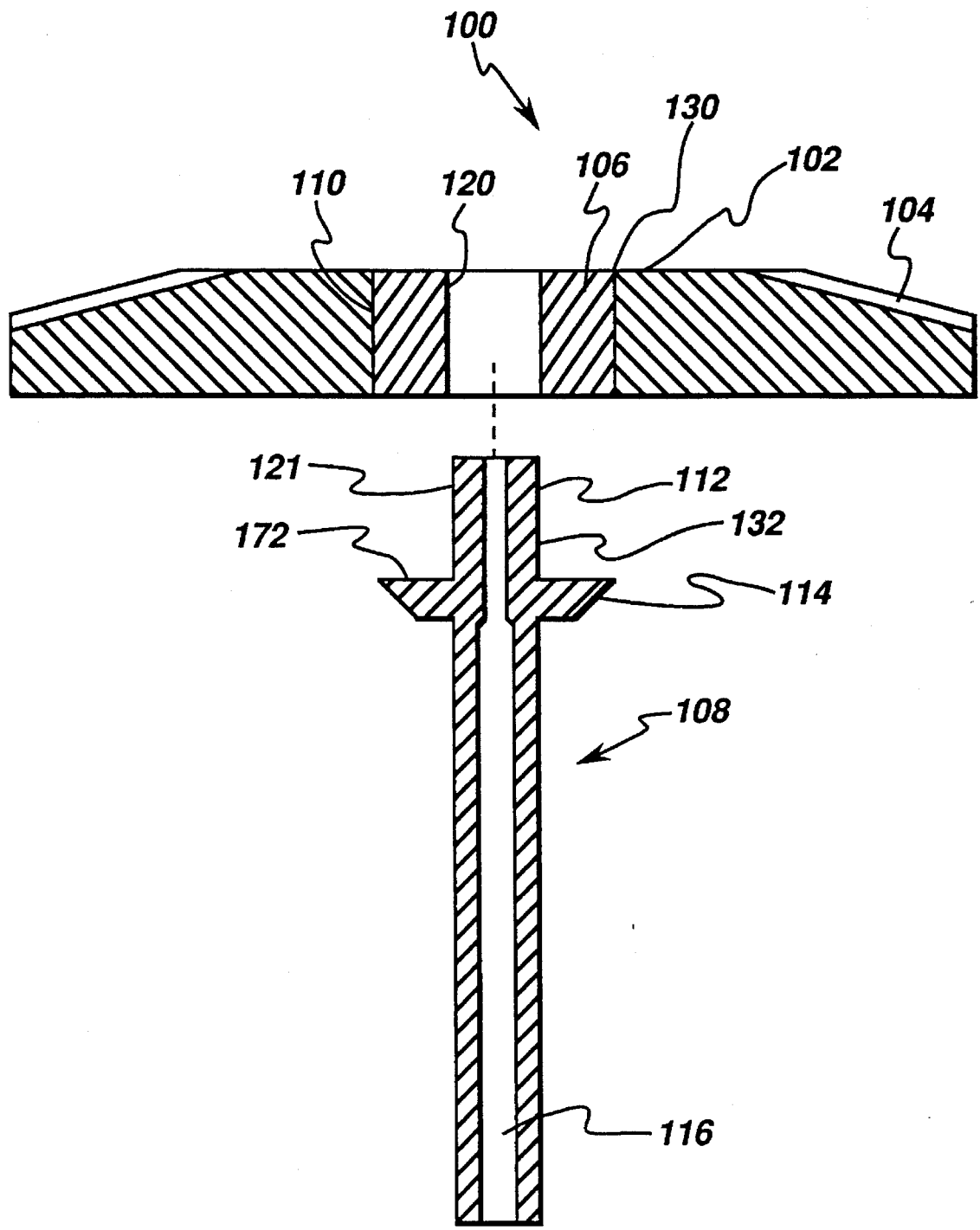
FIG. 4 is a sectional view of one embodiment of an x-ray tube target/stem connection of the present invention.

Referring now to FIG. 4, therein is shown a representative target/stem combination embodying the present invention, in one preferred form thereof, generally designated by the reference numeral 100. The target/stem combination 100 comprises the target 102, preferably made of molybdenum alloy TZM, and, a focal track 104, operatively connected to the target by conventional metallurgical means for reflecting the x-rays generated by the cathode 68 through the window 64 (as shown in FIG. 2). An insert 106 for diffusion bonding to the stem 108 is co-processed with the target 102 during the manufacture thereof. The target is preferably a powder-metallurgy-alloy preferably compatible with all processes used for target manufacture including: powder making, die pressing, sintering, forging, annealing, and coating or brazing to a graphite back (not shown). The insert alloy should also be able to maintain a small grain size, high strength and good ductility during the combination of process steps utilized during the manufacture of the target which includes the insert being operatively connected to the internal portion of the target along seam 110. One such material is tantalum. The insert could also be selected from a group of materials comprising: Ta-10W (Ta, 10W); T-111 (Ta, 8W, 2Hf); T-222 (Ta, 9.6W, 2.4Hf, 0.01C); ASTAR-811C (Ta, 8W, 1Re, 1Hf, 0.025C); GE-473 (Ta, 7W, 3Re); Ta-2.5W (Ta, 2.5W); and Ta-130 (Ta with 50–200 ppm Y) or other metals which meet the above criteria and which can maintain the bond between the stem and the target for at least about 40,000 scan seconds.

The stem 108 is preferably made of Nb and more preferably from a Nb-based alloy chosen from the group comprising: CB-752 (Nb, 10W, 2.5Zr); C129Y (Nb, 10W, 10Hf, 0.1Y); FS-85 (Nb, 28Ta, 11W, 0.8Zr); C103 (Nb, 10, Hf, 1Ti, 0.7Zr), of which C103 is most preferred, or other metals which can maintain the bond between the stem and the target for at least about 40,000 scan seconds when used as described above.

The stem end 112 which would make contact with the insert 106 is slightly tapered as is the insert 106. This tapering is to facilitate press fitting the stem 108 into the insert 106 so that sufficient pressure between the two for diffusion bonding is provided. The stem 108 may have a flange 114 which also diffusion bonds with insert 106. The stem may also have a hollow center 116 to reduce the conduction of heat down the stem to the rotor and bearings.

One advantage of the materials for both the stem and the insert mentioned above is that the coefficient of thermal expansion of the stem material is greater than the coefficient of thermal expansion of the insert material which is in turn greater than the coefficient of thermal expansion of the target material. In order to achieve effective diffusion bonding between all three components, intimate contact between adjacent components at the temperature for diffusion bonding is required. The differences in the coefficients of thermal expansion stated above at diffusion bonding temperatures result in a compressive pressure between the components (stem, insert and target) thereby ensuring the necessary intimate contact.

As illustrated in FIG. 4, the connection along seam 110 and between walls 120, 121 and 122 provides for a unitary construction of target 102 and stem 106 which is more resistant to structural changes during the stressing caused by the above mentioned severe protocol uses. Since it has been determined that the imbalance problems were, most likely, caused by changes that occur in the area of the target/stem attachment, the illustrated constructions are believed to at least reduce the relative changes in position between the stem and target thereby significantly reducing the rotor imbalance problems.

While the articles contained herein constitute preferred embodiments of the invention, it is to be understood that the invention is not limited to these precise articles, and that changes may be made therein without departing from the scope of the invention which is defined in the appended claims.

What is claimed is:

1. An x-ray tube comprising:
   an envelope;
   a cathode, operatively positioned in the envelope;
   an anode assembly including a rotor and a stator, operatively positioned relative to the rotor; and
   a target, operatively positioned relative to the cathode and operatively connected to the rotor by metal to metal diffusion bonding between the target and a metal insert and metal to metal bonding of the insert to a stem, wherein the coefficient of thermal expansion of the stem material is greater than the coefficient of thermal expansion of the insert material which is in turn greater than the coefficient of thermal expansion of the target material.

2. The x-ray tube of claim 1, wherein at least about 40,000 x-ray scan-seconds are completed prior to failure by anode assembly imbalance.

3. The x-ray tube of claim 1, wherein the stem is diffusion bonded to the insert.

4. The x-ray tube of claim 3, wherein the insert comprises a tantalum alloy.

5. The x-ray tube of claim 3, wherein the insert comprises a material chosen from the group consisting of:
   Ta; Ta-10W (Ta, 10W); T-111 (Ta, 8W, 2Hf); T-222 (Ta, 9.6W, 2.4Hf, 0.01C); ASTAR-811C (Ta, 8W, 1Re, 1Hf, 0.025C); GE-473 (Ta, 7W, 3Re); Ta-2.5W (Ta, 2.5W); and Ta-130 (Ta with 50–200 ppm Y).

6. The x-ray tube of claim 3, wherein the stem comprises a Nb alloy.

7. The x-ray tube of claim 3, wherein the stem comprises a material chosen from the group consisting of:
   Nb; CB-752 (Nb, 10W, 2.5Zr); C129Y (Nb, 10W, 10Hf, 0.1Y); FS-85 (Nb, 28Ta, 11W, 0.8Zr); and C103 (Nb, 10, Hf, 1Ti, 0.7Zr).

8. The x-ray tube of claim 3, wherein the stem comprises C-103.

9. An x-ray system comprising:
   an enclosure;
   at least one cooling means, operatively connected to the enclosure, for cooling the system;
   an x-ray tube, operatively positioned inside the enclosure, for generating and directing x-rays toward a target, the x-ray tube comprising:
   an envelope;
   a cathode, operatively positioned in the envelope;
   an anode assembly including a rotor and a stator, operatively positioned relative to the rotor; and
   a target, operatively positioned relative to the cathode and operatively connected to the rotor by metal to metal diffusion bonding between the target and a metal insert and metal to metal bonding between the insert and a stem, wherein the coefficient of thermal expansion of the stem material is greater than the coefficient of thermal expansion of the insert material which is in turn greater than the coefficient of thermal expansion of the target material.

10. The x-ray system of claim 9, wherein at least about 40,000 x-ray scan-seconds are completed prior to failure by anode assembly imbalance.

11. The x-ray system of claim 9, wherein the stem is diffusion bonded to the insert.

12. The x-ray system of claim 9, wherein the insert comprises a tantalum alloy.

13. The x-ray system of claim 9, wherein the insert comprises a material chosen from the group consisting of:
   Ta; Ta-10W (Ta, 10W); T-111 (Ta, 8W, 2Hf); T-222 (Ta, 9.6W, 2.4Hf, 0.01C); ASTAR-811C (Ta, 8W, 1Re, 1Hf, 0.025C); GE-473 (Ta, 7W, 3Re) Ta-2.5W (Ta, 2.5W); and Ta-130 (Ta with 50–200 ppm Y).

14. The x-ray system of claim 13, wherein the stem comprises C-103.

15. The x-ray system of claim 9, wherein the stem comprises a niobium alloy.

16. The x-ray system of claim 9, wherein the stem comprises a material chosen from the group consisting of:
   Nb; CB-752 (Nb, 10W, 2.5Zr); C129Y (Nb, 10W, 10Hf, 0.1Y); FS-85 (Nb, 28Ta, 11W, 0.8Zr); and C103 (Nb, 10, Hf, 1Ti, 0.7Zr).

17. An x-ray tube having a combination of target and stem comprising:
   a target operatively connected to a stem by metal to metal diffusion bonding between the target and a metal insert and metal to metal bonding between the insert and the stem, the target being made of a molybdenum alloy and the stem being made of a Nb alloy;
   wherein the coefficient of thermal expansion of the stem material is greater than the coefficient of thermal expansion of the insert material which is in turn greater than the coefficient of thermal expansion of the target material.

18. The combination of claim 17, wherein the insert comprises a tantalum alloy.

19. The combination of claim 17, wherein the insert comprises a material chosen from the group comprising:
   Ta; Ta-10W (Ta, 10W); T-111 (Ta, 8W, 2Hf); T-222 (Ta, 9.6W, 2.4Hf, 0.01C); ASTAR-811C (Ta, 8W, 1Re, 1Hf, 0.025C); GE-473 (Ta, 7W, 3Re); Ta-2.5W (Ta, 2.5W); and Ta-130 (Ta with 50–200 ppm Y).

20. The combination of claim 17, wherein the stem comprises a material chosen from the group comprising:
   Nb; CB-752 (Nb, 10W, 2.5Zr); C129Y (Nb, 10W, 10Hf, 0.1Y); FS-85 (Nb, 28Ta, 11W, 0.8Zr); and C103 (Nb, 10, Hf, 1Ti, 0.7Zr).

21. The combination of claim 17, wherein the stem comprises C-103.

22. An x-ray tube comprising:
   an envelope;
   a cathode, operatively positioned in the envelope;
   an anode assembly including a rotor and a stator, operatively positioned relative to the rotor; and
   a target, operatively positioned relative to the cathode and operatively connected to the rotor by metal to metal diffusion bonding between the target and a metal insert and metal to metal bonding of the insert to a stem, wherein the stem comprises a Nb alloy; and wherein the coefficient of thermal expansion of the stem material is greater than the coefficient of thermal expansion of the insert material which is in turn greater than the coefficient of thermal expansion of the target material.

23. An x-ray system comprising;

an enclosure;

at least one cooling means, operatively connected to the enclosure, for cooling the system;

an x-ray tube, operatively positioned inside the enclosure, for generating and directing x-rays toward a target, the x-ray tube comprising:

an envelope;

a cathode, operatively positioned in the envelope;

an anode assembly including a rotor and a stator, operatively positioned relative to the rotor; and a target, operatively positioned relative to the cathode and operatively connected to the rotor by metal to metal diffusion bonding between the target and a metal insert and metal to metal bonding between the insert and a stem, wherein the stem comprises a niobium alloy; and wherein the coefficient of thermal expansion of the stem material is greater than the coefficient of thermal expansion of the insert material which is in turn greater than the coefficient of thermal expansion of the target material.

* * * * *